(12) United States Patent
Wang

(10) Patent No.: US 10,846,520 B2
(45) Date of Patent: Nov. 24, 2020

(54) SIMULATED SANDTRAY SYSTEM

(71) Applicant: Zi-Nan Wang, Dalian (CN)

(72) Inventor: Zi-Nan Wang, Dalian (CN)

( * ) Notice: Subject to any disclaimer, the term of this patent is extended or adjusted under 35 U.S.C. 154(b) by 378 days.

(21) Appl. No.: 15/951,193

(22) Filed: Apr. 12, 2018

(65) Prior Publication Data

US 2019/0180089 A1 Jun. 13, 2019

(30) Foreign Application Priority Data

Dec. 12, 2017 (CN) .......................... 2017 1 1316947

(51) Int. Cl.
*G06K 9/00* (2006.01)
*H04N 5/225* (2006.01)
*G06F 3/0484* (2013.01)
*A61B 5/16* (2006.01)
*G06F 3/0481* (2013.01)
*G09B 9/00* (2006.01)

(52) U.S. Cl.
CPC .......... *G06K 9/00335* (2013.01); *A61B 5/165* (2013.01); *G06F 3/04815* (2013.01); *G06F 3/04842* (2013.01); *G06K 9/00671* (2013.01); *G09B 9/00* (2013.01); *H04N 5/225* (2013.01)

(58) Field of Classification Search
CPC .. G06K 9/00335; G06K 9/00671; G06K 9/00; A61B 5/165; A61B 5/16; G06F 3/04815; G06F 3/04842; G06F 3/04; G09B 9/00; H04N 5/225
See application file for complete search history.

(56) References Cited

U.S. PATENT DOCUMENTS 10,203,762 B2 * 2/2019 Bradski .................. G02B 30/52

* cited by examiner

*Primary Examiner* — Timothy A Musselman

(57) ABSTRACT

The simulated sandtray system consists of camera device, controller, digital processor, display device, physical sandtray mark, and physical sand cabinet mark. Camera devices are linked with digital processor and display device. Physical sandtray mark is connected to cameral devices for the purpose of delivering optical information. Physical sand cabinet mark is linked to camera devices for the purpose of delivering optical information. The advantages and features of this invention are as follows: a number of initiators, online connection and simultaneous inter-regional operation of 3D virtual sandtray.

11 Claims, 2 Drawing Sheets

SIMULATED SANDTRAY SYSTEM

TECHNICAL FIELD

Figure 1:
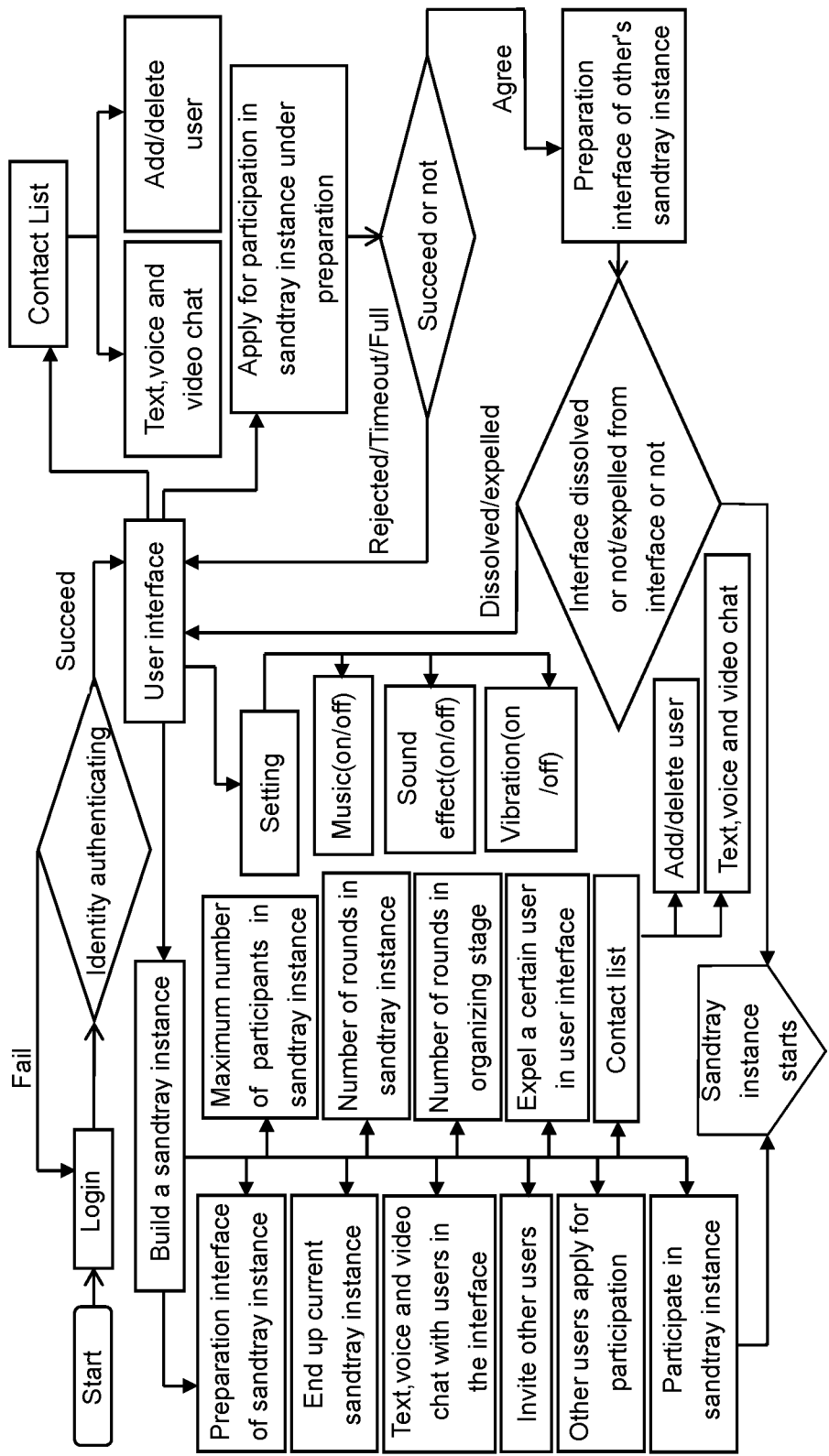

This invention is a kind of simulated sandtray system involving psychological knowledge. To be specific, it is a simulated sandtray system built based on the practices and development of sandplay theories in psychology.

TECHNICAL BACKGROUND

The continuous development of sandplay theories has given rise to physical sandtray that consists of group sandtray and individual sandtray. As compared with the characteristics of individual sandtray, group sandtray plays an effective role in improving interpersonal relationships and facilitating the development of groups and individuals. Generally speaking, restrictive group sandtray is a preferred choice. Without special requirements for establishment of sandplay room, restrictive group sandtray refers to a group sandplay method restricted by certain rules and following the same conditions as individual sandtray does. Group members may give rise to a sequence in a random way according to the agreed method. In a round where group members get a sequence, they are not allowed to exchange or interact with each other linguistically or non-linguistically. Consultants may discover the personal traits of every group member according to their compliance with rules.

Restrictive group sandtray is suitable for treatment of interpersonal relationships, conjugal relationships and relationships between children and parents. Restrictive sandplay is an epitome of social reality, and group sandtray can reflect everyone's behavioral patterns. In group sandplay, everyone has their ideas, which, however, should be integrated together when they are required to complete the same work. Meanwhile, in sandplay, consultants may observe everyone's personal traits and help them understand their own traits. Sandplay can only attain the goal of final integration after multiple production processes and continuous adjustments.

Technical Problems

It is difficult to promote the use of physical sandtray in practices because of the problems like fixed location of sandtray's consulting room, large size of physical sandtray, a limited number of participants and models, operator's inflexible operation schedule, and no sound or smell in operation. All these problems should be emphatically addressed.

Technical Solutions

This invention is a kind of simulated sandtray system. Transplantation of group sandtray to electronic device can solve a series of problems-consultants' incapability of dealing with numbers of users at a time, address of sandtray room, and large size of sandtray room. As compared with physical sandtray, virtual sandtray ensures not only more flexible operations but also broader spatial expansion and functional extension. Instead of facing spatial constraints, virtual sand cabinet is customizable. Its model has unified styles and scale standards that can make itself more representative. Operation of virtual sandtray can lead to more vibration feedbacks of equipment. Meanwhile, electronic sandtray can display the lighting effects that cannot be created by physical sandtray. Every mold of sandtray performs the behavior with their unique characteristics, and virtual sandtray sees a change in climate and natural cycle of day and night. The same molds can be used repeatedly and shown by sandtray. In operation, individual and group sandtrays are free from the influence of consultants' spirit, energy and organizational capacity. In this way, users may devote full attention to sandtray operation, which can improve user's perception and help them observe and perceive the sandtray and its model in an all-round way. In virtual environment, users can get rid of the constraints of physical rules in real world under a specific situation, and then, they can operate the sandtray and its model from all directions. As compared with physical sandtray which requires an assistant to deal with sandtray data statistics, virtual sandtray can digitally process the data and information in sandtray operation through its system.

Technical Solution Adopted:

The simulated sandtray system consists of camera device, controller, digital processor, display device, physical sandtray mark, and physical sand cabinet mark. The camera devices include mobile phone, tablet, laptop, smart glasses, BlueCam and other devices that can be used to capture real scenes. The controller is constituted by motion capture lever and other handheld devices that can show user behaviors through sensor. Camera devices and controller are connected to digital processor and display device. Real scenes can be captured by camera devices, and real scene data captured can be received, analyzed and digitally processed by the digital processor linked to camera devices and controller. Afterwards, the aforesaid data will be displayed by display device, and interact with equipment which is furnished with this invention through the internet, local area network or other internet connection modes. Physical sandtray mark means that when real sandtray is considered unsuitable in real environment for a variety reasons, certain marks such as pictures, plastics, cloth or other objects this invention recognizes as effective marks can be used for virtual sandtray mapping. Optical information can be delivered when these marks are connected with camera devices. Physical sand cabinet mark means that when the real environment cannot accommodate a real cabinet for a variety of reasons, certain marks such as pictures, plastics, cloth or other objects this invention recognizes as effective marks can be used for virtual sand-cabinet mapping. Optical information can be delivered when these marks are connected with camera devices.

Sense of smell: When certain requirements are satisfied, the external devices of the equipment authenticated by this invention will emit harmless gas. Below is the specific process: to obtain basic parameters of the virtual smell that is going to be emitted in the virtual environment; to produce control signals according to the aforementioned basic parameters as well as the layout and performance parameters of smell generator; and to control smell generator with control signals so that smell generator can generate the smell corresponding to the virtual smell. To obtain the basic parameters of the virtual smell that is going to be emitted in the virtual environment means analyzing the pre-stored virtual data to generate basic data set; and deriving basic parameters from basic data set according to time parameters of virtual smell when the virtual smell is going to be emitted in the virtual environment. After obtaining basic parameters of the virtual smell going to be emitted in the virtual environment, there is a need to work out real smell parameters in the real environment. To produce control signals according to basic parameters as well as layout and performance parameters of smell generator means producing control signals in line with real smell parameters, basic parameters, and layout and performance parameters of smell generator. To control smell generator with control signals so that smell generator can generate the smell corresponding to the virtual smell means that when the smell generator is controlled by control signals, the real smell corresponding to the virtual smell will be emitted and then blew by fan.

Sense of touch: touch effect is simulated through equipment vibration. Scene layout can enhance the feeling of test subject. The combination between virtuality and reality may lead to more obvious test effects, which can provide basic conditions for more test modes and make them available. Below is the specific process: to obtain the state information of every object in virtual reality and/or the environment where the test subject stays; to get tactile feedback information in line with state information; and to give tactile feedback in light of tactile feedback information. The state information of every object obtained in virtual reality scenes and/or the environment where the test subject stays includes physical state information of every object identified in virtual reality and the motion state information of every object monitored in the environment where the test subject stays through the preset radar sensor or infrared sensor. The physical state information refers to object's hardness and/or roughness. The motion state information includes location, moving direction, and/or moving speed. If the state information refers to motion state information, the tactile feedback information will be the distance between test subject and object in the environment where the test subject stays, which is determined according to the motion state information of every object. If the distance between test subject and object in the environment where the test subject stays is greater than 0, feedback intensity information corresponding to every object can be obtained according to the correlation between the preset distance and feedback intensity. Tactile feedback given to test subject in line with tactile feedback information includes the pressure which is imposed on test subject by pressure device and corresponds to feedback intensity information, and/or the vibration which is imposed on test subject by vibration device and corresponds to feedback intensity information. If the state information means physical state information, the tactile feedback information will involve the tactile perceptual information of every object generated according to every object's physical state information displayed by the preset touch screen in virtual reality. The tactile perceptual information refers to hardness of every object touched, regional distribution information and/or magnitude of force required by roughness. The tactile feedbacks given to test subject in line with tactile feedback information consist of input voltage signal input into sending and receiving electrodes according to the tactile perceptual information and predetermined matching rules in different areas of touch screen; electrostatic force of every area produced according to different input voltage signals; and hardness and/or roughness of every object touched when the electrostatic force of every area is produced. Before giving tactile feedbacks to test subject in line with tactile feedback information, the pressure that the test subject imposes on touch screen needs to be tested. When the aforementioned pressure is greater than the preset threshold value, touch screen will give tactile feedbacks to test subject according to tactile feedback information.

Sandtray setting: after camera device is focused on physical sandtray or physical sandtray mark, virtual sandtray will appear in the scene of camera device, and virtual sandtray model will be shown according to characteristics of physical sandtray or physical sandtray mark. On the condition of physical sandtray, virtual sandtray not only completely falls within the plane of physical sandtray but also extends to the space that cannot be operated by real sandtray. The space mentioned above includes the top and bottom of real sandtray. It is a virtual sandtray which has a spatial extension within the largest plane section of real sandtray. On the condition of physical sandtray mark, virtual sandtray appears in the device only based on sandtray mark. Both physical sandtray and sandtray mark provide references for viewfinder, because physical sandtray and sandtray mark coexisting can switch to each other. As compared with physical sandtray which faces a restriction, virtual sandtray shows its own particularity in terms of attributes—dynamic and changeable form as well as the air, ground and underground. The difference between sandtray and sand-cabinet is that after sandtray setting, the form of virtual sandtray may undergo dynamic changes actively or passively, whereas virtual sand cabinet has no interactions among the air, ground and underground.

Sand cabinet setting: after the camera device is focused on physical cabinet or physical cabinet mark, the virtual cabinet will appear in the scene of the device, and then, it will be displayed according to the physical cabinet or physical cabinet mark. On the condition of physical cabinet, all sand tools will be shown in physical cabinet in a more obvious way. On the condition of physical cabinet mark, a completely virtual cabinet will be re-created according to physical cabinet mark.

Specific operations: the interacting distance in augmented reality or virtual reality can be changed by adjusting the distance between camera device and real object or mark, or by zooming in or out with controller, gesture or finger. The observational focus position in augmented reality or virtual reality can be changed by altering the focus position of camera device or by zooming in or out with controller, gesture or finger. Changes in angle of camera device relative to reality may lead to a different observational angle in augmented reality or virtual reality. All operations in augmented reality are conducted on device's screen. Virtual sand cabinet can carry out the operations like rotation, reverse, stretch, translation, replacement, and transformation. After sand tools are obtained from sand cabinet, camera device needs to be moved into sandtray and the virtual sandtray with sand tools can be observed. Sand tools can be placed in the sandtray or given up. If sand tools need to be put in the virtual sandtray, hands should be moved away within virtual sandtray, whereas if sand tools need to be given away, hands should be moved away outside virtual sandtray. Camera device can demonstrate that sand tools are superposed on physical sandtray. Multi-user networked operations can be conducted by AR, VR and other devices through local area network or the internet.

In the test process, organizers or relevant staff may be required to provide guidance or communicate with others in virtual scene. The implementation methods adopted by this invention are as follows: virtual reality platform receives communication request message from the first virtual reality device, the communication request message including FPV (first person view) location information and sign of the second virtual reality device; the FPV location information refers to any visual angle information of the first virtual reality information in panoramic visual angle location information; according to the FPV location information and the sign of the second virtual reality device, the second video zone in panoramic video area of the second virtual reality device can be determined to obtain multidimensional video in the second video zone and send the video to the first virtual reality device for display. The virtual reality platform consists of the processing chips built in or outside the first and second virtual reality devices and used for multidimensional video communications in these devices. Before receiving the communication request message sent by the first virtual reality device, the virtual reality platform receives registration request message sent by the first and second virtual reality devices. The registration request message sent by the first virtual reality device involves the correspondence between panoramic video area and panoramic visual angle location information of the first virtual reality device. The registration request message sent by the second virtual reality device describes the correspondence between panoramic video area and panoramic visual angle location information of the second virtual reality device. It is necessary to build and save the sign of the first virtual reality device as well as the correspondence between panoramic video area and panoramic visual angle location information of the first virtual reality device. There is also a need to build and save the sign of the second virtual reality device as well as the correspondence between panoramic video area and panoramic visual angle location information of the second virtual reality device. The second video zone in the panoramic video area of the second virtual reality device can be determined according to FPV location information and sign of the second virtual reality device. In this process, the second person view (SPV) location information corresponding to the FPV location information in the panoramic visual angle location of the second virtual reality device needs to be determined according to the FPV location information and the sign of second virtual reality device. The SPV location information is any visual angle location information in the panoramic visual angle location information of the second virtual reality device. The second video zone corresponding to the SPV location information in the panoramic video area of the second virtual reality can be determined in the light of SPV location information. The first video zone corresponding to the FPV location information can be determined in the panoramic video area of the first virtual reality device in accordance with FPV location information. The second video zone corresponding to the first video zone can be determined in the panoramic video area of the second virtual reality device according to the sign of the first second virtual reality device and the first video zone. The virtual reality platform receives the images in the panoramic video areas of the first and virtual reality devices. The panoramic multidimensional video of the first virtual reality device can be built in line with the images in the panoramic video area of the first virtual reality device. The panoramic multidimensional video of the second virtual reality device can be built in line with the images in the panoramic video area of the second virtual reality device In the test process, communication with tester may be required. However, the test results may be affected by the complex operations caused by a large number of keys and manual control. In view of this, this invention reduces operations and brings in emotional elements through special setting modes that can weaken the influence of emotions on testers and communicate with testers intelligently. To be specific, the equipment is comprised of mobile voice terminal, virtual environment terminal, and external server. The external server is connected with mobile voice terminal and virtual environment terminal, and the mobile voice terminal linked to virtual environment terminal. The mobile voice terminal is composed of speech acquisition module used to acquire user's speech signals and pre-process the speech signals acquired; speech recognition module aimed at converting pre-processed speech signals into text message and transforming text message into control commands and parameters; extraction module of speech's emotional characteristic parameters intended to extract the parameters with emotional characteristics in pre-processed speech signals of speech acquisition module; memory module used to save speech recognition data loaded and updated through external servers, speech control command database and speech emotion database; wireless communication module aimed at sending the identified control commands and parameters or speech text messages and corresponding speech emotion to virtual environment terminal for the purpose of connecting with external service and loading and updating its data package to memory module; and processor intended to process user's speech message or send update command to external server to load and update the data of memory module. The processor is connected with speech acquisition module, speech recognition module, extraction module of speech's emotional characteristic parameters, memory module, and wireless communication module. The speech acquisition module is linked to speech recognition module and extraction module of speech's emotional characteristic parameters. The emotional characteristics extracted by the extraction module of speech's emotional characteristic parameters are mapped to speech text message identified by speech recognition module. The memory module is linked to speech recognition module and extraction module of speech's emotional characteristic parameters. The virtual environment terminal is comprised of memory unit used to save model bases of virtual character's emotional expressions and actions loaded and updated through external server as well as intonation and speech speed databases corresponding to speech emotion; and the communication module aimed at communicating with mobile speech terminal and linked with external server so that the database of external server can be loaded and updated in the memory unit. The memory unit is connected with speech broadcasting module and display module. The speech acquisition module is mainly composed of microphone. The speech recognition module consists of speech characteristic extraction unit, speech characteristic comparison unit, and comparison result output unit. The speech characteristic extraction unit is connected with speech characteristic comparison unit which is linked to comparison result output unit. The extraction module of speech's emotional characteristic parameter is constituted by extraction unit of emotional characteristic, comparison unit of emotional characteristic, and output unit of emotional characteristic. The extraction unit of emotional characteristic is linked with comparison unit of emotional characteristic that is connected to output unit of emotional characteristic. The speech broadcasting module is composed of intonation match unit and speech broadcasting unit, and the intonation match unit is connected with speech broadcasting unit. The display module is comprised of action match unit and display unit that are linked with each other. The method involves the steps below: after mobile speech terminal is successfully connected with virtual environment terminal, processor of mobile speech terminal and virtual environment terminal will send query command of database version to external server. The query command is aimed at checking whether the versions of speech recognition data, speech control command database and speech emotion database in memory module of mobile speech terminal, plus the model bases of virtual character's emotional expressions and actions in memory unit of virtual environment terminal, are consistent with those in external server. If there is a difference between them, the latest data of external server should be loaded and updated in memory module and unit so as to ensure the up-to-date data are saved in memory module and unit. Speech acquisition module gathers user's speech signals and sends these signals to speech recognition module and extraction module of speech's emotional characteristic parameter after they are pre-processed by the methods like filtering and quantifying. Speech recognition module, plus speech recognition data saved in memory module, converts speech signals pre-processed into text message and match text message with command data in speech control command database to work out whether the message is control command. If the text message is control command, corresponding control command and parameter will be generated and outputted to the virtual environment terminal for the sake of control operation; provided the text message is not a control command, it will be considered as speech message. The extraction module of speech's emotional characteristic parameter will analyze the waveform of the pre-processed speech signals and extract the parameters with emotional characteristics. Such parameters will be matched with emotional data in speech emotion database to work out corresponding emotional characteristics. Afterwards, the emotional characteristic information will be mapped to corresponding words or sentences. The words and sentences to which emotional characteristic and emotional characteristic information are mapped will be sent to virtual environment terminal. The action match unit of virtual environment terminal will match the emotional characteristic received with the model bases of virtual character's emotional expressions and actions in memory unit to obtain the emotional expressions and actions corresponding to the emotional characteristic. The emotional expressions and actions can be displayed by display unit. Intonation match unit can match the words or sentences corresponding to the emotional characteristic with the data corresponding to speech emotion in intonation and speech speed database to work out the intonation and speech speed of corresponding words or sentences. The speech message can be played by speech broadcasting unit and display module simultaneously based on a certain intonation and speed to guarantee multiuser communications in real environment.

Software Support:

AR development tools are composed of ARPA, ARLab, DroidAR, Metaio, Wikitude, and vuforia. The development platforms include Android, IOS, GoogleGlass, WindowsPC, Unity, EpsonMoverio BT-2000, Vuzix M-100, Optinvent OPA1, PhoneGap, Titanium, and Xamarin.

VR development tools are composed of HoloLens Emulator, Google VR SDK, Google VR View, Web VR, Cardboard SDK, Faceshift Studio, A-Frame, Oculus DK2, Cryengine, Destinations Workshop Tools, RealSense SDK, Leap Motion SDK, kinect SDK, Source Engine, OpenVR SDK, Oculus SDK, Gear VR, and Nibiru VR SDK. Development platforms are comprised of Android, IOS, GoogleGlass, WindowsPC, Unity, EpsonMoverio BT-2000, Vuzix M-100, Optinvent OPA1, PhoneGap, Titanium, Xamarin, Auto Stingray3D, Gamebryo, and Virtools.

This invention opens and observes virtual sandtray through camera device. The bluetooth unit in camera device is separable from camera device and able to increase interactive operations in augmented or virtual reality. The authentication equipment of this invention is furnished with responsive switch that can give rise to a smell.

Application of this Invention:

This invention should be started up to enter main interface. People logging into this main interface have two identities when operating sandtray instance: organizer or initiator (both are called organizer below) and invitee, namely, ordinary user.

A user who builds a sandtray instance will be deemed as organizer, and all other users entering this sandtray instance will be considered as invitees.

Organizer may establish a sandtray instance without including other users. On this occasion, the sandtray instance will be defined as individual sandtray.

When organizer builds a new sandtray instance and sends an invitation, online users in its contact list or people nearby located through LBS (location-based service) will be invited for multiuser sandtray operations.

Invitee may send a request for the purpose of participating in a sandtray instance under preparation.

The functions in the preparation interface:

Organizer can view its contact list.

The list of online users nearby can be viewed based on LBS.

The number of people operating group sandtray can be selected and sandtray instance can be modified before start.

All invitees accepting the invitation can be communicated through text, voice or video chat or private letter.

All invitees rejecting the invitation can be communicated through text, voice or video chat in a private way.

The number of sandtray operation rounds can be determined, and sandtray instance can be modified arbitrarily before start.

The number of sandtray organizing rounds can be determined and sandtray instance can be modified arbitrarily before start.

The preparation interface can be closed or concealed.

Other Feasible Operations.

Contact List

All people are allowed to add contacts in contact list, through which the online state of contacts can be checked. Online state includes "waiting, away from keyboard, in preparation, and full (only shown to organizer)". In sandtray, both organizer and invitees can view the tag of contacts, with the tag including icon, name, remark and other tabs. Clicking the tab of contacts can demonstrate more details of contacts.

About "Waiting":

It means that organizer is filing an application or invitees are being invited.

About "Away from Keyboard"

It means that no actions have been performed by organizer or invitee during a period of time, including text, voice and video chat, entry into sandtray instance that hasn't been started, invitation or application, and the state before "away from keyboard" will resume when any interface operation is conducted.

About "in Preparation"

It means that organizer builds a sandtray instance that hasn't started or filled up or invitees have entered a sandtray instance that hasn't been started.

About "Full"

This state can be only seen by organizer. When the sandtray instance which hasn't started has filled up, other invitees will be not allowed to apply for participation and organizer will not be permitted to invite other people either.

About "in Sandtray"

It means that organizer and invitees have entered a sandtray instance that has started. At this moment, neither application nor invitation is permitted.

Restriction on the Number of Participants Operating Group Sandtray:

Organizer needs to select 1-100 participants for group sandtray instance, and number of participants can be changed before start. A failure will be caused if the number of participants after changes is smaller than the number of people that have taken part in the sandtray instance.

About how to Select Number of Sandtray Operation Rounds

Organizer is required to determine the number of operation rounds after building a sandtray instance. Most of the time, the number of operation rounds should be 5 or 8.

About how to Select Number of Organizing Rounds

The number of organizing rounds should be 1-5, which can be altered before start of sandtray instance.

About Tag/Tab

After establishment of sandtray instance, its system will allocates a tag to every user in the preparation interface, with the tag including head portrait, name and color block. This tag can show more detailed information after being clicked.

About Invitation

Only organizer are allowed to send an invitation, and only users online can be invited. Invitees should not be included in the sandtray instance that has started, but they are permitted to enter the preparation interface of other organizer. After sending an invitation, organizer needs to wait for invitee's response. Invitees can reject or agree to accept the invitation during a certain period of time or system will help invitees reject the invitation when time's up.

About Expel

Organizer may ask a certain invitee to leave from the sandtray instance that hasn't started.

About Invitees in Invitation:

Invitees may wait for invitation of organizer.

About Application

Invitees may apply for participation in a certain organizer's sandtray instance that hasn't started, but the organizer needs to stay in the state of "in preparation". The organizer needs to select "agree" or "reject" within a certain period of time, or system will select "reject" automatically when time is up. Organizer who receives applications of several people at a time may approve the applications out of order. Other applications will be invalid when sandtray instance cannot accommodate any people.

About Communication

In a sandtray instance that hasn't started, invitees may have a text, voice and video chat with other people. Besides, everyone is allowed to have a text, voice and video chat with people in contact list.

Other Descriptions on Group Sandtray:

Invitees are allowed to leave from the sandtray instance under preparation.

If organizer starts a sandtray instance that hasn't filled up, it will be considered as individual sandtray, and the organizer will be deemed as sandtray operator.

Organizer may invite several people to participant in sandtray instance at a time and the number of participants can be greater than that limited by sandtray instance.

Invitees enter sandtray instance according to the order set by organizer. After the sandtray instance has filled up, other invitees will not be allowed to enter the sandtray instance and the organizer will not be permitted to send a new invitation either.

Invitees may apply for participation in sandtray instances of several organizers at a time. Application could not be sent if an organizer's sandtray instance has filled up. Invitees may enter sandtray instance of the organizer who gives consent first. After invitees enter a certain organizer's sandtray instance, other applications will be invalid.

Invitees can receive an invitation from several organizers at a time, whereas after they enter a certain sandtray instance, the applications sent and other invitations will be invalid.

Invitees who enter preparation interface of a certain sandtray instance can check the number of rounds and contact list of the sandtray instance as well as communicate with others through text, voice and video chat.

If invitees who have entered a sandtray instance are offline, the sandtray instance will have an unoccupied seat.

If organizer is offline, the sandtray instance will be dissolved and the preparation interface of invitees in the sandtray instance will be closed.

After the sandtray instance fills up, organizer can start sandtray instance with a countdown. After countdown, all people will close the preparation interface and enter a virtual sandtray instance that has started after loading.

Modules of Sandtray Instance

About Sandtray Room

It is also called virtual sandtray room. In virtual reality, real sandtray room is used for production as a prototype. In such environment, the sandtray room is equipped with sandtray, sand cabinet, model and other articles required by real sandtray. As for group sandtray instance, there will be a need for images of other people. In augmented reality, user's room or space can be used without being influenced by address or space size.

About Sand Tool

Sand tool is called model as well. The model which allows operator's imagination to run free can be created based on concise design after analyzing color prototype of different sand tools. The main sand tools consist of human characters, animals, plants, buildings, furniture, articles for daily use, transportation devices, foods, stones, shells, natural substances, climate and others.

About Sand Cabinet.

Sand cabinet is also virtual sand cabinet, which is used to place models. At the beginning, all model operations need to be extracted from sand cabinet, and some other operations are also required to start in the cabinet.

About Sandtray

It is also virtual sandtray, which is used to place and operate sand tools. There are a number of sandtray styles, which can be used to dig out and pile up sand as well as to display water and grass.

About Climate

Climate changes in sandtray instance can be altered.

About Visual Angle

Sandtray instance can be observed from different directions by changing visual angle and height.

About Interface Operation

The sandtray operation data can be recorded by interface in place of consultants. In group sandtray instance, instant communications with other users are permitted.

All people entering the sandtray need to carry out operations with hand, finger, gesture or controller.

In sandtray instance, there is operation state and view state.

About View State

All users can view the whole picture of the sandtray by way of rotation, including close shot and long shot. They can also switch between ordinary visual angle and vertical visual angle through switch and move within the allowable scope of virtual sandtray room to observe and operate the sandtray at any time. Local sandtray can be viewed by zooming in or out with magnifying glasses.

About Operation State

In operation state, sandtray and model operations can be performed, including model placement and operations after model placement. A model will show operation state after being selected. In operation state, model operations like move, rotate, zoom out and delete can be conducted. When sandtray operations such as dig and pile are performed, sound effects will be produced and electronic equipment will also vibrate. If a place of sandtray is dug to a certain depth, there will be some water in the sandtray. When the depth of water reaches a certain degree, the action "dig" will not continue. When the sand piled up in sandtray becomes a high hill that reaches a certain height, the action "pile" will stop. All operations are controlled by equipment's switch. As regards representation mode, handheld devices may be transformed into hands or other assistive devices.

Objective Environment in the Air

Meteorological manifestation mode in sandtray can be changed.

Placement of Operation Models:

Model can be fetched from cabinet in the scene and the placed in sandtray. When placed, the model in sandtray can be edited.

Operations of Model Selected:

The triggered operation of the model that needs operating should be performed with finger, hand or controller to activate the selected state of the model.

Movement of Model Operated

When the model that needs moving is manipulated, it will change with movement of finger, hand or controller.

Rotation of Model Operated

After selection of the model that needs to rotate, it can rotate as finger, hand or controller moves Zoom-Out of Model Operated Operations should be performed with two fingers, hands or controllers for the sake of relative or reverse movements and then mapped to the model Deletion of Model Operated The model are moved out of sandtray Interface Operation Control over music, sound effect, vibration and chat window can be exercised by viewing help interface or shifting to main interface.

Communication:

In group sandtray instance, chat window allows organizer to communicate with invitee privately and all people to communicate with each other. In sandtray instance, organizer's interface has a small window describing "number of invitees+1". Communication can be carried out in not only a public window for all people also a small window for private chat.

In group sandtray instance, organizer may communicate with invitees through text, voice and video chat. Upon the start of sandtray instance, there will be a hint for confirmation in every round, which is used to confirm "start" by invitees. Only when all people have confirmed "start", will next operation be performed. Organizer's interface will show whether all invitees have confirmed "start". Organizer should have a chat with the invitee privately if he hasn't confirmed "start". During operation of group sandtray, system will determine the operation sequence of invitees randomly before the first round, and in this sandtray instance, the operation sequence should remain unchanged.

Explanations on Countdown and Operation Node

If it is a certain invitee's turn to perform an operation, a obvious hint will appear in the screen, and countdown will begin. If there is time limit for operation in every round, every invitee can perform an effective operation or continuously effective operations before the countdown clock hits zero. On the condition of one operation, screen will show the name of next operator after operation. On the condition of disconnected operations, the screen will show the name of next operator if operation stops before countdown clock ends or it will present the name of next operator automatically after the countdown ends. If there are no subsequent operators, it means that the sandtray instance is trapped in a node state. At this point, the screen of every operator will pop up a window, which requires the operator to make supplementary explanations on operation of current round and why such operation is performed in the form of text, voice and video. There is a time limit on supplementary operation. When the countdown ends, the information typed in will be submitted no matter whether the operator has finished making supplementary explanations. The operator is allowed to give up supplementary explanation as well. In the node where a round ends, organizer's interface will only display sandtray instance. Before the countdown ends, organizer can get a screenshot from any angle. The end of countdown means the end of operations in current round and the start of next round. The sandtray instance will be repeated in this way. After the last round, interface of every operator in group sandtray will pop up a independent window in which the sandtray instance can be named based on text, voice and video. There is also countdown for this link. No matter whether the sandtray instance has been given a name or not after countdown, the names of all people will be presented in the interface of every user, which will be sequenced according to operator's operation sequence. The operator needs to select the name for the sandtray instance by way of voting. Finally, the name with the most votes will be selected. If there are names with the same number of votes, the one which wins most votes first will be chosen. On the condition of individual sandtray, user will be prompted to name the sandtray instance independently.

After naming, every operator will be prompted to select their favorite region or model from current sandtray instance. Meanwhile, the screen will pop up a window for supplementary explanations on why they select such region or model. Countdown is also designed for this operation. After countdown, final selection will be recorded. Operator is allowed to give up making selections or supplementary explanations, and the supplementary explanations can be made through text, voice and video.

Upon selection of their favorite operation, every operator will be prompted to choose the model they care about most. Meanwhile, the screen will pop up a window for supplementary explanations on why they care about such model. Countdown is also designed for this operation. After countdown, final selection will be recorded. Operator is allowed to give up making selections or supplementary explanations, and the supplementary explanations can be made through text, voice and video.

Upon selection of the model they care about, every operator will be promoted to select the model or sandtray region they dislike most. Meanwhile, the screen will pop up a window for supplementary explanations on why they dislike such model and region. Countdown is also designed for this operation. After countdown, final selection will be recorded. Operator is allowed to give up making selections or supplementary explanations, and the supplementary explanations can be made through text, voice and video.

Upon recording the operation they dislike most, every operator will select self-image, and the screen will pop up a window for supplementary explanations on why they select such self-image. The supplementary explanations can be made through text, voice and video.

When operators select their favorite region or model, the model they care about most, the model or sandtray region they dislike most and self-image, organizer's interface will display sandtray instance only. Before the end of countdown, organizer may get a screenshot from any angle.

Upon selection of self-image, sandtray instance will be organized. According to the operator's operation sequence above, everyone is permitted to make adjustments within a short time, and countdown is also designed for this stage, where operator can perform any operations on sandtray instance. The number of operation rounds is determined by organizer in the preparation interface of sandtray instance.

Beneficial Results

Multiple initiators and network connection permit inter-regional operation of 3D virtual sandtray

FIGURE EXPLANATION

Figure 2:
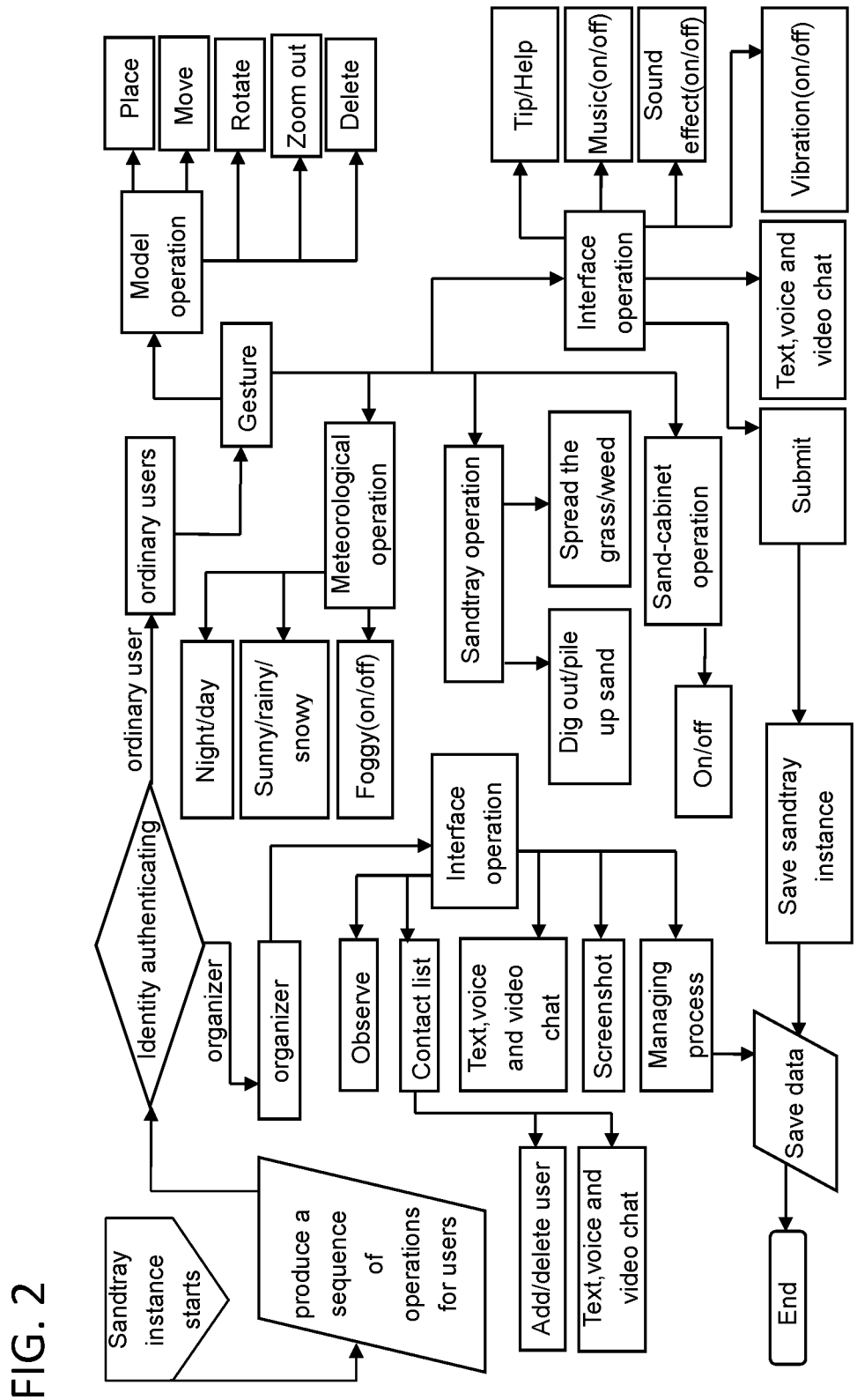

FIG. 1 shows the operating procedures of this invention
FIG. 2 depicts the second part of the operation flowchart of this invention

THE BEST IMPLEMENTATION MODE OF THIS INVENTION

The simulated sandtray system consists of camera device, controller, digital processor, display device, physical sandtray mark, and physical sand cabinet mark. The camera devices include mobile phone, tablet, laptop, smart glasses, BlueCam and other devices used to capture real scenes. The controller is constituted by motion capture lever and other handheld devices that can map user behaviors through sensor. Camera devices and controller are connected to digital processor and display device. Real scenes can be captured by camera devices, and real scene data captured can be received, analyzed and digitally processed by the digital processor linked to camera devices and controller. Afterwards, the aforesaid data will be displayed by display device, and interact with equipment which is furnished with this invention through the internet, local area network or other internet connection modes. Physical sandtray mark means that when real sandtray cannot be placed in real environment for a variety reasons, certain marks such as pictures, plastics, cloth or other objects this invention recognizes as effective marks can be used for virtual sandtray mapping. Optical information can be delivered when these marks are connected with camera devices. Physical sand cabinet mark means that when the real environment cannot accommodate a real cabinet for a variety of reasons, certain marks such as pictures, plastics, cloth or other objects this invention recognizes as effective marks can be used for virtual sand-cabinet mapping. Optical information can be delivered when these marks are connected with camera devices.

Implementation Mode of this Invention

According to description of this invention, the "install", "link" and "connect" should be understood in a broad sense unless otherwise specified and restricted. For example, it can be construed as fixed connection, dismountable connection; one-piece connection refers to mechanical connection, electric connection, direct connection, indirect connection, and two-component interconnection. Ordinary technicians in this field can understand the meanings of the aforementioned terms in this invention under specific situations. In addition, unless otherwise explained, multi- or several described by this invention means no less than two.

If there are no descriptions like individual, group and multiple or several, the operating steps of sandtray instance will always apply no matter whether there are the definitions like one or several users.

To facilitate an understanding of this invention, the effective implementation modes are proposed. This invention can be implemented in various other ways in addition to those described by this invention. The aim of these implementation modes is to ensure more thorough and comprehensive understanding of the public contents in this invention. It is worthwhile to explain that a component which is said to be fixed to another component is likely to be placed on the component or included in the component. When a component is considered to be linked with another component, it may be directly linked to the component or simultaneously included in the component. The terms like vertical, horizontal, left and right aimed at making an explanation are not the only implementation modes. Unless otherwise defined, all technical and scientific terms used herein have the same meanings understood by technicians in the technical field of this invention. The terms of this invention's specification are intended to describe the specific implementation modes rather than to restrict this invention. The terms "and" and "or" used herein include any or all combinations of one or more relevant items listed.

The simulated sandtray system consists of camera device, controller, digital processor, display device, physical sandtray mark, and physical sand cabinet mark. The camera devices include mobile phone, tablet, laptop, smart glasses, BlueCam and other devices used to capture real scenes. The controller is constituted by motion capture lever and other handheld devices that can map user behaviors through sensor. Camera devices and controller are connected to digital processor and display device. Real scenes can be captured by camera devices, and real scene data captured can be received, analyzed and digitally processed by the digital processor linked to camera devices and controller. Afterwards, the aforesaid data will be displayed by display device, and interact with equipment which is furnished with this invention through the internet, local area network or other internet connection modes. Physical sandtray mark means that when real sandtray cannot be placed in real environment for a variety reasons, certain marks such as pictures, plastics, cloth or other objects this invention recognizes as effective marks can be used for virtual sandtray mapping. Optical information can be delivered when these marks are connected with camera devices. Physical sand cabinet mark means that when the real environment cannot accommodate a real cabinet for a variety of reasons, certain marks such as pictures, plastics, cloth or other objects this invention recognizes as effective marks can be used for virtual sand-cabinet mapping. Optical information can be delivered when these marks are connected with camera devices.

The invention and its implementation modes are described as above. Such description which is not restrictive only touches upon one of this invention's implementation modes, but this will not impose restrictions on actual structure. In short, if ordinary technicians in this field design the structural schemes and implementation cases similar to the technical solutions described herein on the premise of adhering to the aim of this invention under the inspiration of this invention, they will be considered within the protected scope of this invention despite the lack of inventor's permission.

INDUSTRIAL APPLICABILITY

According to existing physical rules, real natural environment can be simulated in a complete virtual environment so that operator can perceive the environment through sense of sight, sense of touch, sense of taste, sense of smell and movements, and have a sense of presence in the real environment. The operator will give feedbacks and responses when interacting with virtual environment. Despite the lack of participants, virtual environment is characterized by independence and diversity, and all the information in the virtual sandtray can be digitally processed.

On the other hand, the sandtray information (like image, voice, sense of smell and sense of touch) that cannot be perceived within a certain space-time scope in real world. In this invention, simulation is followed by superposition and the virtual information needs to be applied to real sandtray, which can be perceived by human's organ and provide sensory experience beyond reality. The real environment and virtual object added to the same sandtray can coexist.

The invention claimed is:
1. A simulated sandtray system comprising:
camera devices, wherein the camera devices are configured to capture real scenses;
a controller, wherein the controller comprises a motion capture lever and other handheld devices for mapping user's behaviors through sensor;
a digital processor, wherein the digital processor is linked to the camera devices and the controller, and the digital processor receive, analyzed and digitally processed real scene data captured by the camera device;
a display device, wherein the camera devices and the controller are connected to the digital processer and the display device, the display device is configured to display the real scene data;
physical sandtray mark, wherein the physical sandtray mark is configured to for virtual sandtray mapping when real sandtray cannot be placed in real environment for a variety reasons, and the physical sandtray mark is connected with the camera devices for delivering optical information;
cabinet mark, wherein the cabinet mark is configured for virtual sand cabinet mapping when the real environment cannot accommodate a real cabinet for a variety of reasons, and the cabinet mark is connected with camera devices for delivering optical information; and
wherein simulated sandtray system further comprises an external device, when certain requirements are satisfied, the external device emit harmless gas to simulate real smell environment.
2. The simulated sandtray system according to claim 1, wherein the digital processor obtain basic parameters of the virtual smell that is going to be emitted in the virtual environment, and produce control signals according to the parameters as well as the layout and performance parameters of the external device, and the external device generate the smell according to the basic parameters of the virtual smell.
3. The simulated sandtray system according to claim 1, wherein the simulated sandtray system simulates a touch effect through an equipment vibration of the external device.
4. The simulated sandtray system according to claim 3, wherein the digital processor obtain the state information of object in virtual reality and/or the environment, get tactile feedback information in line with state information, and give tactile feedback in light of tactile feedback information.
5. The simulated sandtray system according to claim 3, wherein the statement information comprises physical state information and motion state information, the physical state information comprises object's hardness and/or roughness, the motion state information comprises location, moving direction, and/or moving speed.
6. The simulated sandtray system according to claim 1, wherein after the camera device is focused on physical cabinet or physical cabinet mark, the virtual cabinet will appear in the scene of the external device, the virtual cabinet is displayed according to the physical cabinet or physical cabinet mark, on the condition of physical cabinet, all sand tools will be shown in physical cabinet in a more obvious way, and on the condition of physical cabinet mark, a completely virtual cabinet will be re-created according to physical cabinet mark.
7. The simulated sandtray system according to claim 1, wherein after the camera device is focused on physical cabinet or physical cabinet mark, the virtual cabinet will appear in the scene of the device, the virtual cabinet will be displayed according to the physical cabinet or physical cabinet mark, on the condition of physical cabinet, all sand tools will be shown in physical cabinet in a more obvious way, and on the condition of physical cabinet mark, a completely virtual cabinet will be re-created according to physical cabinet mark.
8. The simulated sandtray system according to claim 1, wherein the simulated sandtray system can simulate climate change, and the climate changes in sandtray instance can be altered.
9. The simulated sandtray system according to claim 8, wherein sandtray instance can be observed from different directions by changing visual angle and height.
10. The simulated sandtray system according to claim 1, wherein sandtray operation data can be recorded by interface in place of consultants, in group sandtray instance, instant communications with other users are permitted.
11. The simulated sandtray system according to claim 1, wherein the whole picture of the sandtray by way of rotation to be viewed, and ordinary visual angle and vertical visual angle through switch and move within the allowable scope of virtual sandtray room to observe and operate the sandtray at any time.

* * * * *